United States Patent [19]

Saville

[11] Patent Number: Plant 6,808

[45] Date of Patent: May 23, 1989

[54] ROSE PLANT NAMED SAVADAY

[75] Inventor: F. Harmon Saville, Rowley, Mass.

[73] Assignee: Nor'East Miniature Roses, Inc., Rowley, Mass.

[21] Appl. No.: 118,621

[22] Filed: Nov. 9, 1987

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new unusual Mars Orange colored miniature rose.

1 Drawing Sheet

1

The present invention relates to a new and distinct variety of rose plant of the miniature rose class, which was originated by my crossing as seed and pollen parents two unnamed, unpatented seedlings of my creation. The denomination of this new rose is "Savaday".

Among the novel characteristics possessed by this new variety which distinguish it from its parents and all other varieties of which I am aware are its unusual Mars orange colored flowers in this class of rose. Flowers are long lasting on the plant and after cutting. Asexual reproduction by budding of the new variety as performed in Essex County, Mass. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "146C" is plate 146C of The Royal Horticultural Society Colour Chart.

Parentage: Seedling.

*Seed parent.*—Unnamed seedling.

*Pollen parent.*—Unnamed seedling.

Class: Miniature.

The following observations are made of specimens grown outdoors in Essex County, Mass., during the month of July.

FLOWER

Blooming habit: Nearly continuous.

A. Bud:

(1) *Size.*—Medium.

(2) *Form.*—Ovoid.

(3) *Color.*—As sepals first divide, bud color is near 10B flushed with 32B to 32C.

(4) *Sepals.*—Slightly longer than bud, simple.

(5) *Peduncle.*—Length — about ¾ inch. Aspect — straight. Strength — erect. Color — near 144B.

B. Bloom:

(1) *Size.*—Average size when fully expanded — about 1½ inches.

2

(2) *Borne.*—Singly, one to a stem.

(3) *Form.*—High centered at first, becoming flat. Outer petals reflex and quill to points; inner petals roll under; petals have pointed apices.

(4) *Petalage.*—Number of petals under normal conditions — about 28 to 32.

(5) *Color.*—After sepals fall and petals unfurl, petal undersurface which may be seen in pale yellow approaching near 13C to 13D with Nasturtium red color washing near 33C. Orange red coloring may also be seen in washing on top surface of outer petals but coloring of petal top surface is nearer Mars orange 31C but with tonality range of Brick red 35C to D at darkest tone to near Peach 29D. General tonality may be near Mars Orange 31C to 31D. Petal reverse (undersurface) picks up yellow coloring which may also be seen near point of petal attachment on petal top surface.

C. Petals:

(1) *Texture.*—Average.

(2) *Appearance.*—Inside velvety and outside satiny.

(3) *Form.*—Broad, fan shaped with pointed apices.

(4) *Arrangement.*—Regularly arranged.

(5) *Petaloids in center.*—Few.

(6) *Persistence.*—Drop off cleanly, but late.

(7) *Fragrance.*—None.

(8) *Lasting quality.*—Average.

REPRODUCTIVE ORGANS

A. Stamens, filaments and anthers:

*Arrangement and color.*—Regularly arranged around styles. Color — near 24B.

B. Pollen:

*Color.*—Near 24B.

C. Styles: Medium length.

D. Stigmas:

*Color.*—Near 10C.

E. Hips: None observed.

PLANT

A. Form: Upright, compact.

B. Growth: Very vigorous.

*Height attained.*—About 16 to 18 inches.

C. Foliage: Compound 5 to 7 leaflets.

(1) *Size.*—Medium.

(2) *Quantity.*—Abundant.

(3) *Color.*—New foliage: Upper side — near 146A. Under side — near 138B. Old foliage: Upper side — near 137A. Under side — near to 138B.

(4) *Shape.*—Oval, pointed.

(5) *Texture.*—Upper side is semiglossy; under side is matte.

(6) *Edge.*—Serrate.

(7) *Serration.*—Ordinary.

(8) *Leaf stem.*—Color — near to 146C. Under side — near 146C.

(9) *Stipules.*—Medium length, slightly bearded.

(10) *Resistance to disease.*—Blackspot — Average. Mildew — Average. Rust — Average.

D. Wood:

(1) *New wood.*—Color — near 144A. Bark — smooth.

(2) *Old wood.*—Color — near 138A. Bark — smooth.

E. Thorns:

(1) *Thorns.*—Quantity (main stalk) — ordinary. On laterals from stalk — few. Form — long, thin, straight, pointed. Length — medium. Color — near 182B. Position — irregular.

F. Winter hardiness: Needs protection in severe climates.

I claim:

1. A new and distinct variety of rose plant of the miniature rose class and all the parts thereof, substantially as shown and described, characterized particularly by attractive Mars orange colored flowers which are long lasting on the plant and as cut flowers.

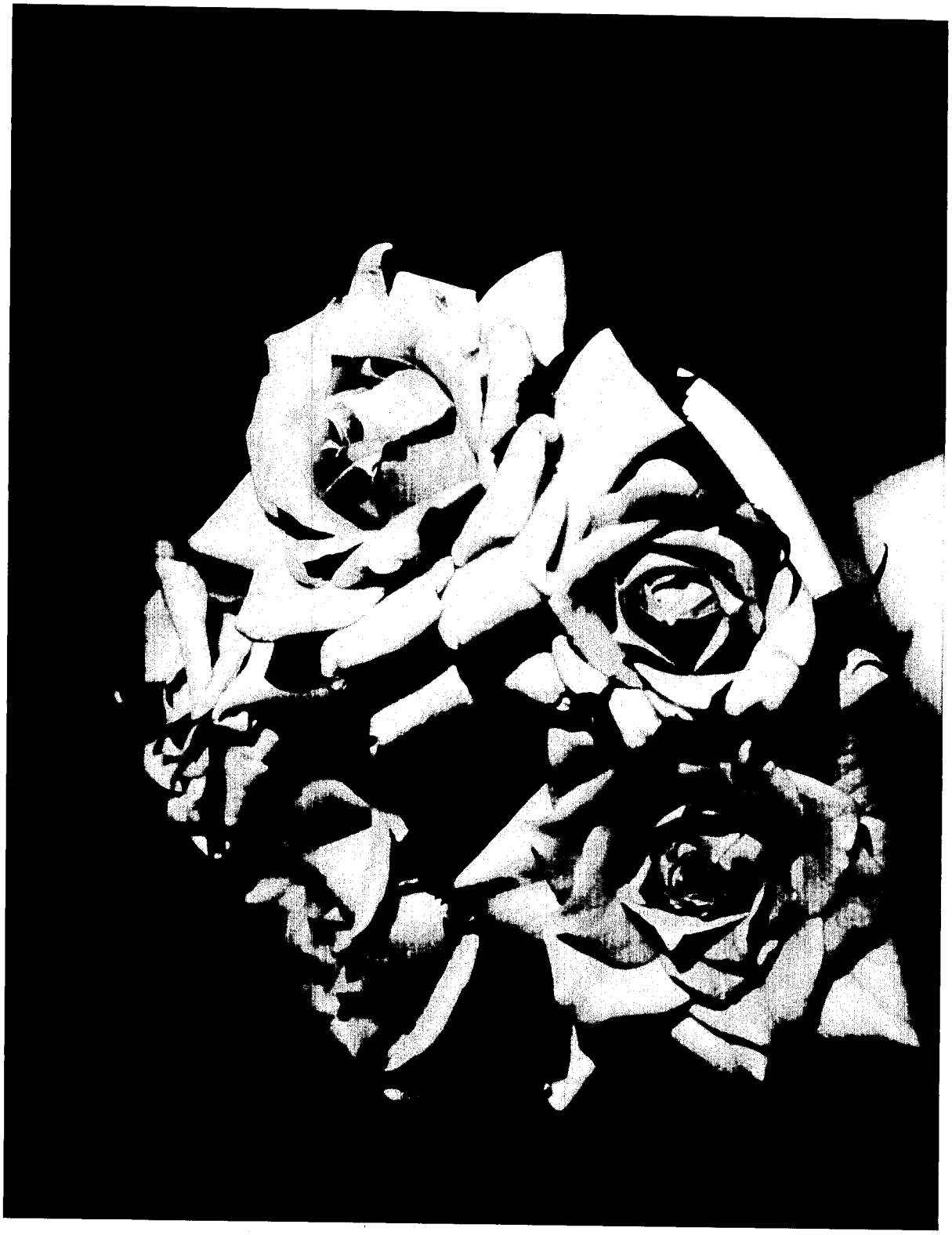

* * * * *